United States Patent
Abbas et al.

(10) Patent No.: US 12,268,470 B2
(45) Date of Patent: *Apr. 8, 2025

(54) TISSUE DETECTION SYSTEM AND METHODS FOR USE THEREOF

(71) Applicant: AI Biomed Corp., Santa Barbara, CA (US)

(72) Inventors: Adnan S. Abbas, Santa Barbara, CA (US); Roshan Shetty, Santa Barbara, CA (US)

(73) Assignee: AI Biomed Corp., Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/493,937

(22) Filed: Oct. 25, 2023

(65) Prior Publication Data

US 2024/0049955 A1 Feb. 15, 2024

Related U.S. Application Data

(63) Continuation of application No. 16/828,803, filed on Mar. 24, 2020, now Pat. No. 11,819,193.

(Continued)

(51) Int. Cl.
*A61B 1/04* (2006.01)
*A61B 1/00* (2006.01)
(Continued)

(52) U.S. Cl.
CPC ........ *A61B 5/0071* (2013.01); *A61B 1/00009* (2013.01); *A61B 1/00042* (2022.02);
(Continued)

(58) Field of Classification Search
CPC ....... A61B 5/0071; A61B 1/042; A61B 1/043; A61B 1/0638; A61B 1/0676; A61B 1/07; A61B 5/4227
See application file for complete search history.

(56) References Cited

U.S. PATENT DOCUMENTS

| | | | |
|---|---|---|---|
| 5,749,830 A | 5/1998 | Kaneko et al. | |
| 6,178,346 B1 | 1/2001 | Amundson et al. | |

(Continued)

FOREIGN PATENT DOCUMENTS

| | | |
|---|---|---|
| CN | 1263261 A | 8/2000 |
| CN | 201821335 U | 5/2011 |

(Continued)

OTHER PUBLICATIONS

China Second Office Action CN202080013628.9, dated Apr. 29, 2024, 11pp.

(Continued)

*Primary Examiner* — Anh Tuan T Nguyen
*Assistant Examiner* — Shankar Raj Ghimire
(74) *Attorney, Agent, or Firm* — Carter, DeLuca & Farrell LLP (57) ABSTRACT

A tissue detection system and methods for use thereof are provided. The tissue detection system facilitates stimulating fluorescence via illumination in an area or areas of interest in the human body, detecting non-visible or not easily visible areas of interest subject to such stimulation, and identifying these areas of interest efficiently. The tissue detection system can employ a probe for facilitating illumination/stimulation of a tissue of interest, at least one emitter for generating radiation applied to the tissue of interest, and at least one detector for capturing radiation for the fluorescing tissues of interest.

12 Claims, 12 Drawing Sheets

Related U.S. Application Data (60) Provisional application No. 62/840,609, filed on Apr. 30, 2019, provisional application No. 62/823,252, filed on Mar. 25, 2019, provisional application No. 62/810,510, filed on Feb. 26, 2019.

(51) Int. Cl.
  *A61B 1/06* (2006.01)
  *A61B 1/07* (2006.01)
  *A61B 5/00* (2006.01)

(52) U.S. Cl.
  CPC .............. *A61B 1/042* (2013.01); *A61B 1/043* (2013.01); *A61B 1/046* (2022.02); *A61B 1/0638* (2013.01); *A61B 1/0676* (2013.01); *A61B 1/07* (2013.01)

(56) References Cited

U.S. PATENT DOCUMENTS

| | | | |
|---|---|---|---|
| 6,364,829 | B1 | 4/2002 | Fulghum |
| 6,422,994 | B1 * | 7/2002 | Kaneko ............ A61B 1/045 600/478 |
| 6,537,211 | B1 * | 3/2003 | Wang ............ A61B 1/0005 600/178 |
| 6,590,651 | B1 | 7/2003 | Bambot et al. |
| 7,778,695 | B2 | 8/2010 | Black et al. |
| 9,114,226 | B1 * | 8/2015 | Lash ............ A61B 5/0084 |
| 9,451,882 | B2 | 9/2016 | Nie et al. |
| 9,687,190 | B2 | 6/2017 | Mahadevan-Jansen et al. |
| 10,154,785 | B2 | 12/2018 | Sachse et al. |
| 10,258,275 | B2 | 4/2019 | Mahadevan-Jansen |
| 10,579,891 | B2 | 3/2020 | Abbas et al. |
| 11,819,193 | B2 | 11/2023 | Abbas et al. |
| 2001/0055462 | A1 | 12/2001 | Seibel |
| 2002/0044279 | A1 | 4/2002 | Khoury |
| 2002/0105505 | A1 | 8/2002 | Sendai |
| 2002/0161282 | A1 | 10/2002 | Fulghum |
| 2002/0177778 | A1 | 11/2002 | Averback et al. |
| 2003/0191368 | A1 | 10/2003 | Wang et al. |
| 2006/0069314 | A1 | 3/2006 | Farr |
| 2006/0082731 | A1 | 4/2006 | Drazic et al. |
| 2007/0248152 | A1 | 10/2007 | Wang et al. |
| 2008/0004533 | A1 | 1/2008 | Jansen et al. |
| 2008/0044146 | A1 | 2/2008 | Weisser et al. |
| 2009/0009595 | A1 | 1/2009 | Ishiwata et al. |
| 2009/0060381 | A1 | 3/2009 | Dunki-Jacobs |
| 2009/0076380 | A1 | 3/2009 | Thierman |
| 2009/0135280 | A1 * | 5/2009 | Johnston ............ A61B 1/3132 348/262 |
| 2009/0137893 | A1 | 5/2009 | Seibel et al. |
| 2009/0303317 | A1 | 12/2009 | Tesar |
| 2010/0051808 | A1 | 3/2010 | Zeman et al. |
| 2010/0222673 | A1 | 9/2010 | Mangat et al. |
| 2010/0228089 | A1 | 9/2010 | Hoffman et al. |
| 2011/0063427 | A1 | 3/2011 | Fengler et al. |
| 2011/0164249 | A1 | 7/2011 | Innami et al. |
| 2011/0190760 | A1 | 8/2011 | Niver et al. |
| 2012/0010483 | A1 | 1/2012 | Mahadevan-Jansen et al. |
| 2012/0059254 | A1 | 3/2012 | Lifan et al. |
| 2012/0268573 | A1 | 10/2012 | Schonborn et al. |
| 2013/0216482 | A1 | 8/2013 | Kwon et al. |
| 2013/0281845 | A1 | 10/2013 | Luiken |
| 2013/0329224 | A1 * | 12/2013 | Takaoka ............ A61B 1/0669 356/402 |
| 2014/0340500 | A1 | 11/2014 | Hoegele |
| 2015/0010878 | A1 | 1/2015 | Seibel et al. |
| 2015/0374452 | A1 | 12/2015 | Saito |
| 2016/0150948 | A1 | 6/2016 | Shimamoto |
| 2017/0046586 | A1 | 2/2017 | Abbas et al. |
| 2017/0065287 | A1 | 3/2017 | Silva et al. |
| 2017/0232119 | A1 | 8/2017 | Kularatne et al. |
| 2017/0236022 | A1 | 8/2017 | Abbas et al. |
| 2018/0070806 | A1 | 3/2018 | Matsuo et al. |
| 2018/0132708 | A1 | 5/2018 | Rizo |
| 2018/0270474 | A1 | 9/2018 | Liu |
| 2020/0397266 | A1 | 12/2020 | Hufford |
| 2021/0038065 | A1 | 2/2021 | Xu et al. |

FOREIGN PATENT DOCUMENTS

| | | | |
|---|---|---|---|
| CN | 102697487 A | 10/2012 | |
| CN | 204462021 U | 7/2015 | |
| CN | 207280928 U | 4/2018 | |
| JP | H07155290 A | 6/1995 | |
| JP | H07155291 A | 6/1995 | |
| JP | H10309282 A | 11/1998 | |
| JP | 4321697 B2 | 8/2009 | |
| WO | WO-2016159073 A1 * | 10/2016 | ......... A61B 1/00009 |
| WO | 2017175374 A1 | 10/2017 | |

OTHER PUBLICATIONS

Japanese Office Action JP2021-549911 dated Jan. 30, 2024, 9pp.
Novel optical approach to the interoperative detection of parathyroideal glands; Paras; 2012. (Year: 2012).
NPL internet search Log; 2019. (Year: 2019).
Liu Gang et al., Raman Spectroscopic Study of Different Human Tissues, Spectroscopy and spectral Analysis, vol. 25, No. 5, 723-725, May 2005. (Year: 2005).
Prosst et al.; "Fluorescence-guided minimally invasive parathyroidectomy; a novel detection techynique for parathyroid glands", Surgical Endoscopy and Other techniques, vol. 20, p. 1488-1492; 2006. (Year: 2006).
Manfait et al., Diagnosis and Prognosis of Tissue Pathologies; Microspectroscopy: An Application to Human Thyroid Tumors, Proceedings of SPIE, vol. 3918, 153-160 (May 2000). (Year: 2000).
Monici et al., "Cell and tissue autofluorescence research and diagnostic appls"; vol. 11, pp. 227-256, 2005. (Year: 2005).
Chinese Office Action issued in corresponding Chinese Application No. 202080013628.9 dated Nov. 22, 2023, 32 pages.
China Third Office Action CN202080013628.9, dated Sep. 30, 2024, 13 pp.
China Office Action 202080013628.9 dated Dec. 16, 2024, 13pp.
European Office Action EP20763150.8 dated Feb. 10, 2025 5pp.

* cited by examiner

TISSUE DETECTION SYSTEM AND METHODS FOR USE THEREOF

CROSS-REFERENCE TO RELATED APPLICATIONS

This application is a continuation of U.S. patent application Ser. No. 16/828,803, filed on Mar. 24, 2020, which claims the benefit of priority to U.S. Provisional Applications Ser. No. 62/810,510 filed Feb. 26, 2019; 62/823,252 filed Mar. 25, 2019; and 62/840,609 filed Apr. 30, 2019, the entire contents of all of which are hereby incorporated by reference in their entirety.

FIELD

The present technology is generally related to a tissue detection system and methods for use thereof for illuminating and stimulating a surgical operating region of interest in a human body that has an area or areas that are not or not easily visible to the human eye, detecting these areas, and efficiently identifying these areas to a user.

BACKGROUND

For many processes, including surgical operations, an area or areas of interest in a region of a human body may not be visible to the eye of a person performing the process, but these areas may be detectable by other means. However, fluorescence can be used to identify areas of a region of a human body including an area or areas of surgical interest. Some materials may exhibit fluorescence at non-visible wavelengths. Other areas of interest may exhibit too low a contrast to the human eye to be easily visible. Therefore, there is a need for a tissue detection system and a method for use thereof for stimulating fluorescence in an area or areas of interest in the human body, detecting non-visible or not easily visible areas of interest subject to such stimulation, and identifying these areas of interest efficiently.

SUMMARY

The techniques of this disclosure generally relate to a tissue detection system and a method for use thereof.

In one aspect, the present disclosure provides a tissue detection system for locally stimulating fluorescence in a surgical region, and locating fluorescing areas in the surgical region, the system including a probe having a distal end, the distal end being configured for placement in contact or near contact with tissue material of interest in the surgical region; at least one emitter and at least one emitter optical fiber, the at least one emitter being configured to emit radiation for stimulating fluorescence in the tissue material of interest, and the at least one emitter optical fiber being coupled to the at least one emitter and extending through at least a portion of the probe; at least one detector and at least one detector optical fiber, the at least one detector being configured to detect fluorescence from the tissue materials in the surgical region of interest, and the at least one detector optical fiber being coupled to the at least one detector, and extending through at least a portion of the probe; a controller and user interface coupled to the emitter and the detector, the controller being configured to initiate operation of the at least one emitter and the at least one detector, and the user interface configured to provide feedback to an operator regarding operation of the tissue detection system; where distal ends of the at least one emitter optical fiber and the at least one detector optical fiber are collocated with the distal end of the probe, the at least one emitter optical fiber is configured to transfer the radiation from the emitter to the distal end thereof, and the at least one detector optical fiber is configured to transfer a signal corresponding to the fluorescence to the detector.

In another aspect, the disclosure provides a tissue detection system for locally stimulating fluorescence in a surgical region, and locating fluorescing areas in the surgical region, the system including a probe having a distal end, the distal end being configured for placement in contact or near contact with tissue material of interest in the surgical region; at least one emitter and at least one emitter optical fiber, the at least one emitter being configured to emit radiation for stimulating fluorescence in tissue material of interest, and the at least one emitter optical fiber being coupled to the at least one emitter and extending through at least a portion of the probe; at least one camera being configured to detect fluorescence from the tissue materials in the surgical region of interest; a controller and user interface coupled to the emitter and the detector, the controller being configured to initiate operation of the at least one emitter and the at least one camera, and the user interface configured to provide feedback to an operator regarding operation of the tissue detection system; where a distal end of the at least one emitter optical fiber is collocated with the distal end of the probe, the at least one emitter optical fiber is configured to transfer the radiation from the emitter to the distal end thereof, the at least one camera is spaced above the surgical region, and the at least one camera detects fluorescence over a wide field of view.

In yet another aspect, the disclosure provides a method of tissue detection and surgery using a tissue detection system, the method including positioning a distal end of a probe of the tissue detection system in contact or near contact with tissue material of interest; generating radiation using at least one emitter, the at least one emitter connected to at least one emitter optical fiber, and the at least one emitter optical fiber extending through at least a portion of the probe to the distal end of the probe; transferring the radiation through the at least one emitter optical fiber to the distal end of the probe positioned in contact or near contact with the tissue material of interest; stimulating fluorescence in the tissue material of interest using the radiation from the at least one emitter at the distal end of the probe; detecting the stimulated fluorescence using at least one detector, the at least one detector connected to at least one detector optical fiber, and the at least one detector optical fiber extending through at least a portion of the probe to the distal end of the probe; identifying the tissue material of interest using the detected, stimulated fluorescence; and removing the tissue material of interest during the surgery after identification of the tissue material of interest.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

As discussed below, devices and methods are provided for stimulating fluorescence via illumination in an area or areas of interest in the human body, detecting non-visible or not easily visible areas of interest subject to such stimulation, and identifying these areas of interest efficiently. A tissue detection system and a method for use of the tissue detection system are used to facilitate such stimulating, detection, and identification. As discussed below, embodiments of the tissue detection system are used to stimulate fluorescence in tissues of interest and detect the fluorescence quickly and conveniently from those tissues of interest.

In some embodiments of the tissue detection system, an emitter and a detector may be placed in direct contact or near contact with potentially fluorescing tissue materials of an area or areas of interest such that the stimulation and detection take place in confined regions. To illustrate, the emitter and the detector can be separate from or part of a probe with or without use of fiber-optics, the probe may be positioned to touch or be brought into close proximity to an area or areas, fluorescence in the area or areas could be stimulated with the emitter, and the fluorescence in the area or areas can be detected by the detector if such fluorescence exceeds a threshold. In some embodiments, the emission and the detection are in near infrared (IR) spectral bands, which can be selected to stimulate and detect fluorescence in, for example, parathyroid tissue.

A method using auto-fluorescence for discriminating parathyroid material from thyroid material or other tissues in a neck region is described in U.S. application Ser. No. 13/065,469, which is incorporated herein by reference in its entirety. U.S. application Ser. No. 13/065,469 discloses that, when exposed to radiation in a narrow wavelength range of about 785 nm, which is just outside visible range, both the thyroid and the parathyroid auto-fluoresce in a wavelength range above 800 nm and sometimes centered at 822 nm. The wavelength range above 800 nm is also not visible, and the intensity of the fluorescence of the parathyroid material is significantly higher than that of the thyroid material.

This difference in the relative amount of fluorescence can be used to discriminate between different tissues (e.g., parathyroid material, thyroid material, and other tissues in the neck region) for surgery. To illustrate, even though the general locations of the parathyroid material are known, the parathyroid material is hard to discriminate accurately enough visually for surgery, and that can be a problem with any surgical procedure that requires identification of the parathyroid material.

Tissue detection systems 10, 10', and 10" and methods for use of the tissue detection systems 10, 10', and 10" disclosed herein can be applicable to surgical procedures that requires identification of tissue. The tissue detection systems 10, 10', and 10" can be used to identify tissues such as, for example, parathyroid material, thyroid material, and other tissues in the neck region to facilitate removal during surgery. In other words, the identification of tissues by the tissue detection systems 10, 10', and 10" allow tissue materials to be identified using an affirmative or negative identification of the tissue. Once identified (via the affirmative or negative identification), the tissue materials can be removed during surgery.

Figure 1:
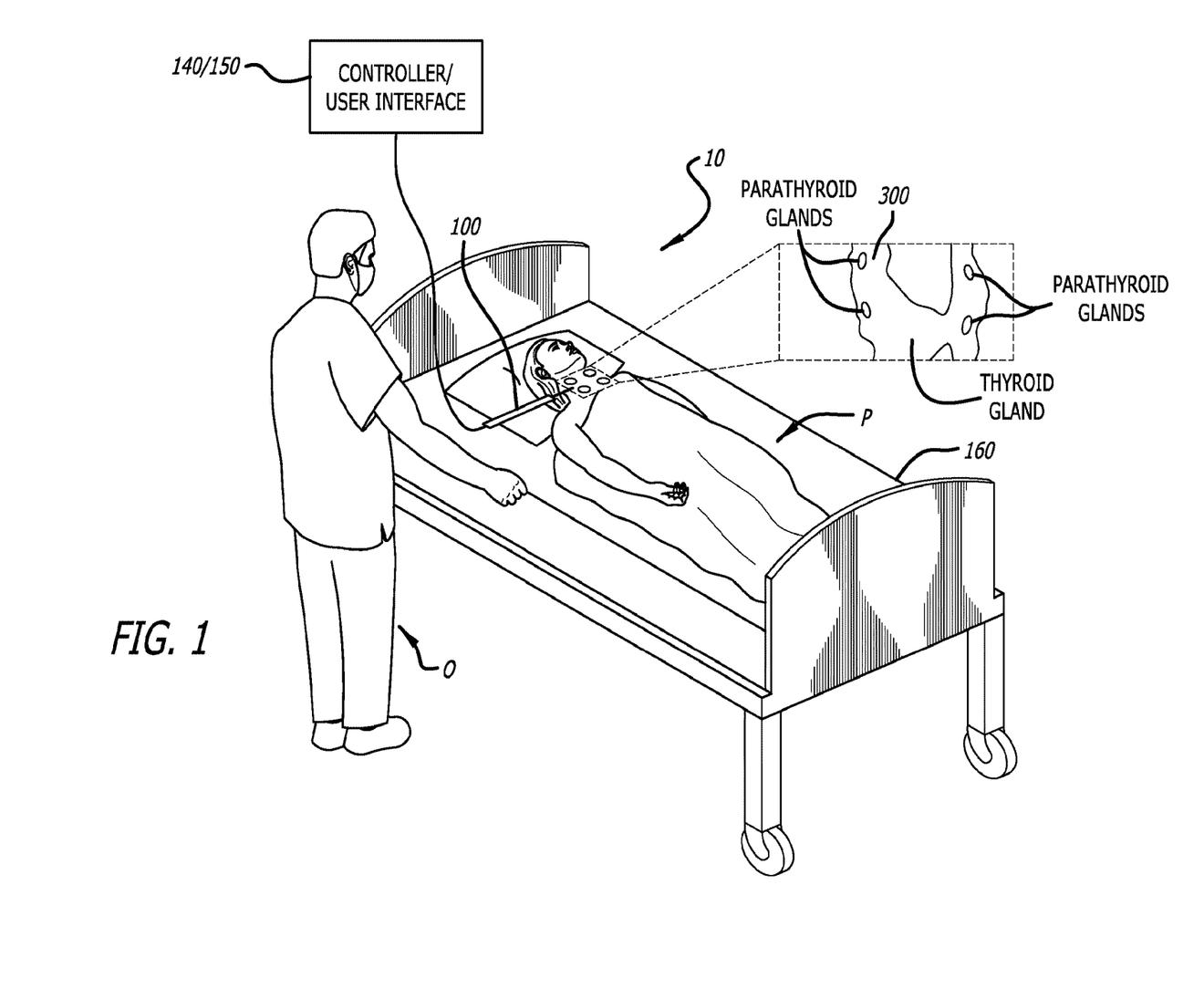
FIG. 1 is an overview of a tissue detection system that illustrates the tissue detection system in relation to a patient and a user, where an internal area of the patient is enlarged and a location of the internal area is indicated for reference.

As depicted in FIG. 1, the tissue detection system 10 includes a probe 100, a controller 140, and a user interface 150. The controller 140 and the user interface 150 can be combined with or be separate from one another, and the controller 140 and/or the user interface 150 can include a display (such as a display 210 from FIGS. 5A and 5B) for displaying images such as, for example, video created through use of the tissue detection system 10.

As depicted in FIG. 1, the probe 100 can be positioned by an operator O relative to a patient P received on a surgical table 160. FIG. 1 depicts the probe 100 being positioned by an operator O during surgery to touch or be brought into close proximity with potentially fluorescing tissue materials such as parathyroid material 300 of the patient P. As such, the tissue detection system 10, according to an embodiment of the current disclosure, may be used to detect (via affirmative or negative identification) the parathyroid material 300 of an exposed internal neck region of the patient P during surgery.

Identification of the parathyroid material 300 is an example of a process where the operator O, for instance, a surgeon, a nurse, a surgical assistant, or other operating room personal can use the tissue detection system 10 to facilitate performance of a surgery on an area or areas of interest, where the area or areas of interest may not be seen by eye. In the case of the identification of the parathyroid material, the parathyroid material fluorescences in the near IR, and thus, is not visible. The intensity of the fluorescence of adjacent thyroid material and other is different than that of the parathyroid materials. Thus, tissue materials that are parathyroid materials (affirmative identification), and tissue materials that are not parathyroid materials (negative identification) can be identified. Thus, using the probe 100 in conjunction with the controller/user interface 140/150 may be used to tactilely identify a region of interest. Particular parameters suitable for parathyroid tissue including stimulation and detection is discussed below, but the basic concepts disclosed would apply to other applications where fluorescence may be stimulated.

Figure 2A:
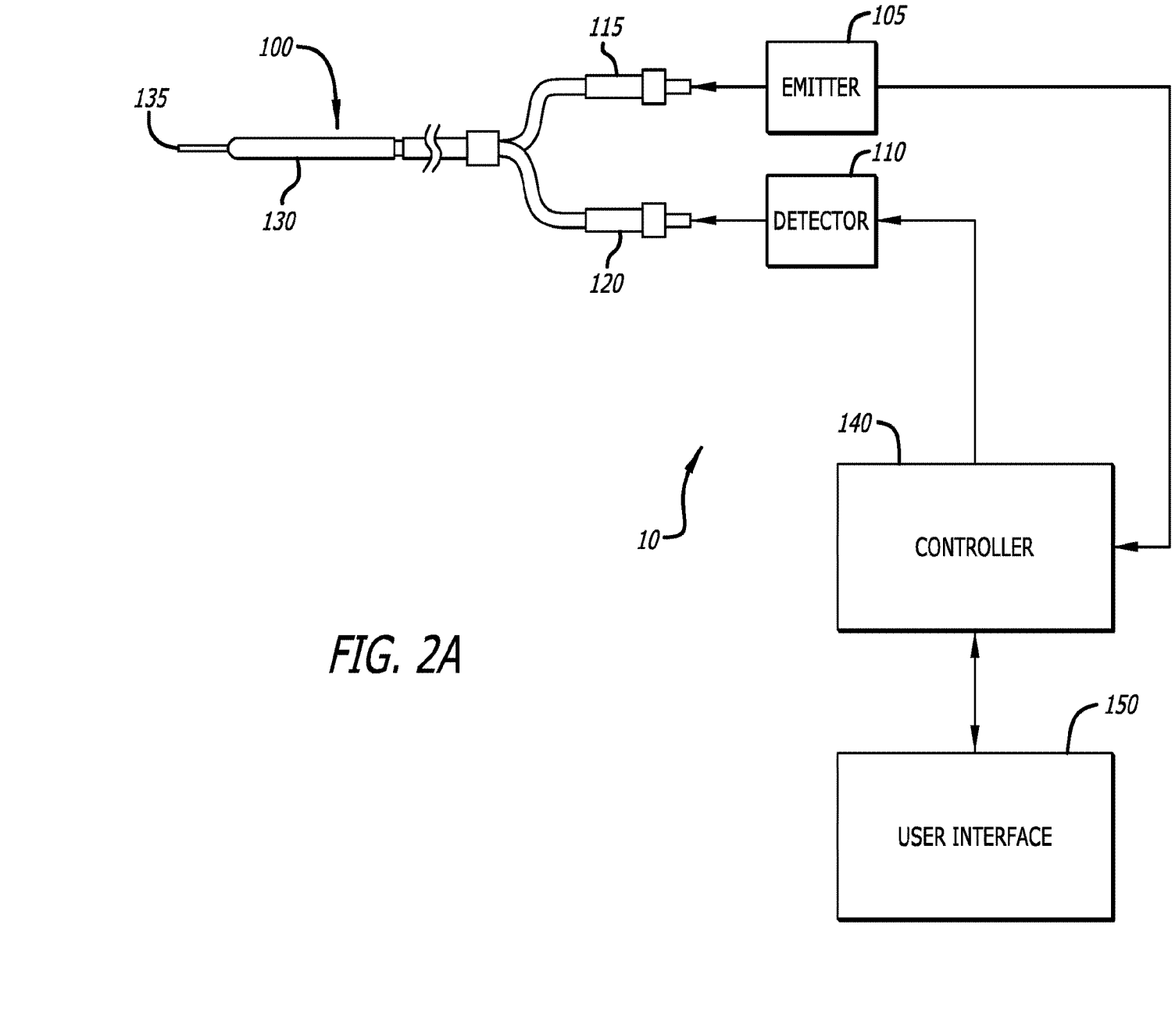
FIG. 2A is a partial block diagram that illustrates the tissue detection.

FIG. 2A depicts additional elements of the tissue detection system 10. The probe 100 may in some embodiments include one or more probe bodies 130 that may be tubular in shape or in some other shape that is conveniently handheld, and that can be made of a variety of possible materials, including metals, plastics, and/or composites among others.

As depicted FIG. 2A, a single probe body 130 is provided, and the tissue detection system 10 also includes an emitter or emitters 105 and a detector or detectors 110 coupled to an emitter optical fiber or fibers 115 and a detector optical fiber or fibers 120, respectively. The emitter 105 can be configured to emit radiation at a selected wavelength to stimulate fluorescence in a region of interest via tuning and/or device selection, and optical elements 125 can be provided to alter the emitted radiation from the emitter 105 lower or higher via filtering. Furthermore, the detector 110 is configured to process radiation captured by the probe 100. In the case of the identification of the parathyroid material, the emitter 105 (with or without use of the optical elements 125) emits radiation at a wavelength of about 785 nm to facilitate auto-fluorescence of the parathyroid material, and the detector 110 is configured to process radiation captured by the probe 100, which for the parathyroid material undergoing auto-fluorescence is at wavelengths ranging from 808-1000 nm.

Figure 2B:
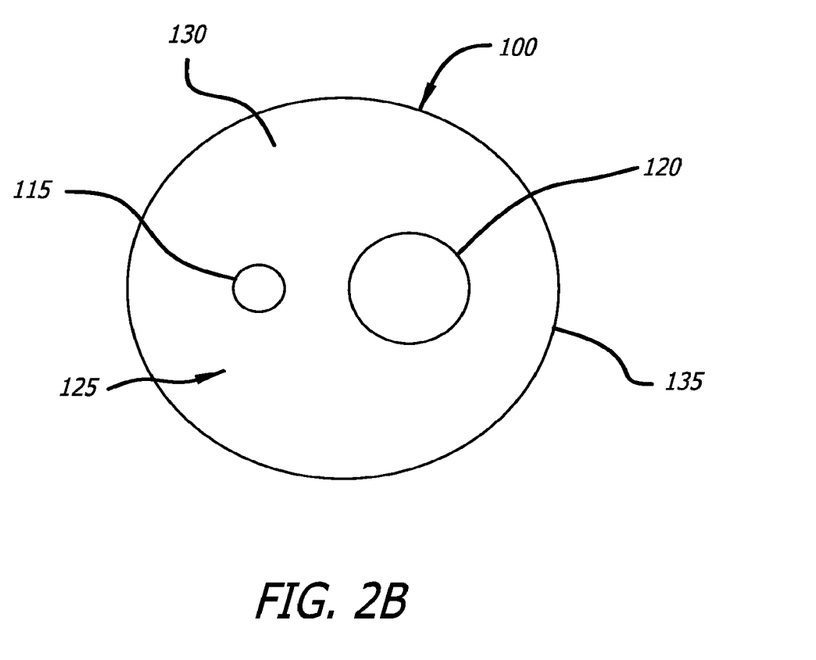
FIG. 2B is an enlarged distal end view of a probe of the tissue detection system of FIG. 2A.

The emitter 105 and the detector 110 can be separate from or part of the probe body 130. And the probe body 130 incudes a distal end 135 (FIG. 2B), at least a portion of the emitter optical fiber or fibers 115 extend through at least the probe body 130 and facilitates transmission of the radiation from the emitter 105 to the distal end 135 of the probe body 130, and at least a portion of the detector optical fiber or fibers 120 extend through at least the probe body 130 and facilitates capture and transmission of radiation from the distal end 135 of the probe body 130 to the detector 110. As depicted in FIG. 2B, the emitter optical fiber or fibers 115 and the detector optical fiber or fibers 120 can terminate at the distal end 135 of the probe body 130. However, other arrangements such as multiple fibers in multiple bundled probe bodies may also be suitable. In any case, the emission and detection fibers can terminate together or close together at the distal end 135 of the probe body 130.

The controller 140 can be used to control transmission of the radiation from the emitter 105 and to control detection of the radiation at the detector 110, and the user interface 150 can be used to interact with and control operation of the controller 140. In use, the emitter 105 (via control using the controller/user interface 140/150) along with the optical element(s) 125 (such as one or optical lenses and/or filters or the like) is configured to deliver radiation chosen to illuminate in order to stimulate fluorescence through the emitter optical fiber or fibers 115 to the distal end 135 of the probe body 130. And in use, the detector 110 (via control using the controller/user interface 140/150) along with the optical element(s) 125 are configured to detect radiation collected at the distal end 135 of the probe body 130 through the detector optical fiber or fibers 120. The optical element(s) 125 provided at the end of the probe body 130 in FIG. 2A, but other arrangements for filtering in the fiber coupling, or emitters and detectors themselves are possible. Furthermore, the user interface 150 may include a switch (not shown) in the form of, for example, a hand or foot switch to initiate the emission of illumination and detection of fluorescence from the emitter 105 and the detector 110, respectively. Furthermore, there may be an audio and/or visual indication that suitable fluorescence signal has been detected.

During use in surgery, the distal end 135 of the probe body 130 is physically brought into contact or near contact (i.e., within at least 1-2 cm) with potentially fluorescing tissue materials of a region of interest within the body, and the operator O through user interface 150 directs the controller 140 to both emit and detect when the distal end 135 of the probe body 130 is in contact or near contact with the surface of the region of interest. Then, a detected fluorescence signal for a tissue of interest is compared to a threshold fluorescence signal for a reference tissue to determine if the detected fluorescence signal is indicative of the presence of the reference tissue. Because the emitter optical fiber or fibers 115 and the detector optical fiber or fibers 120 terminate in a small area at the distal end 135 of the probe body 130 on the order of the size of the fiber end or ends, and because this small area is in contact or near contact with the surface, the area exposed to illumination/stimulation and detection is quite small, thereby allowing for a precise location of the tissue of interest.

In the case of the identification of the parathyroid material, the emitter 105 may be a narrow band source such as a solid state laser, a laser diode, or other suitable source, whose radiation output wavelength through a combination of tuning, device selection, and/or filtering using the optical element(s) 125 is at or near a narrow band around 785 nm. The detector 110 may be an avalanche photodiode or other near IR detector or 2D array of IR detectors, which may be used in concert with demodulation using, for example, a highpass (or longpass) optical filter (of the optical element (s) 125) such that radiation whose wavelength is above the source wavelength (for instance, above 800 nm and ranging from 808-1000 nm) is detected. The radiation wavelength outputted by the emitter 105 (via use of tuning, device selection, and/or filtering using the optical element(s) 125) may be altered lower or higher than that used for identification of the parathyroid material 300 to facilitate identification of other tissue materials.

One of the advantages of touching the surface of the region of interest with the small area at the distal end 135 of the probe body 130 (where emitter optical fiber or fibers 115 and the detector optical fiber or fibers 120 terminate) is that the optical signals are less affected by ambient light, which in the case of an operating room may have a significant amount of near IR components. Immunity to such ambient light may be further increased by modulating the emitter radiation and collecting the fluorescence signal using a phase lock technique, such as lock-in detection or FFT (fast Fourier transform) techniques.

Figure 3A:
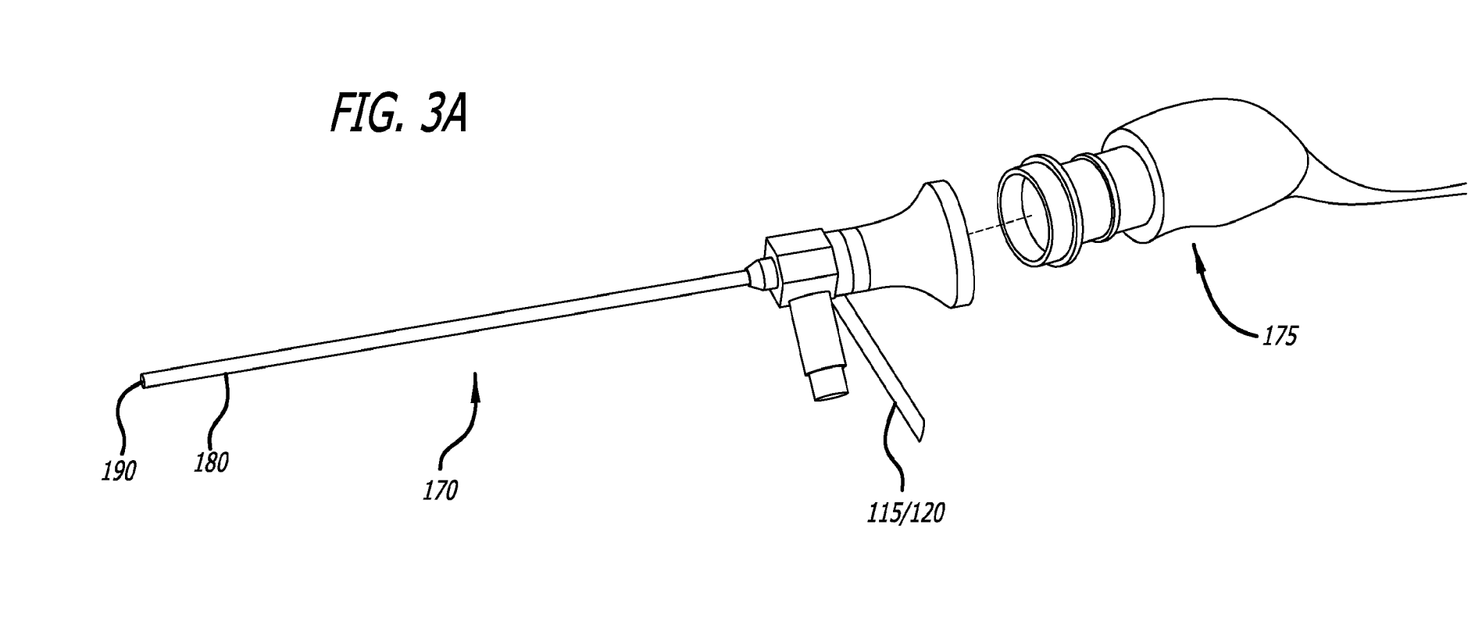
FIG. 3A is a perspective, photographic view that illustrates an endoscopic probe used with the tissue detection system.
Figure 3B:
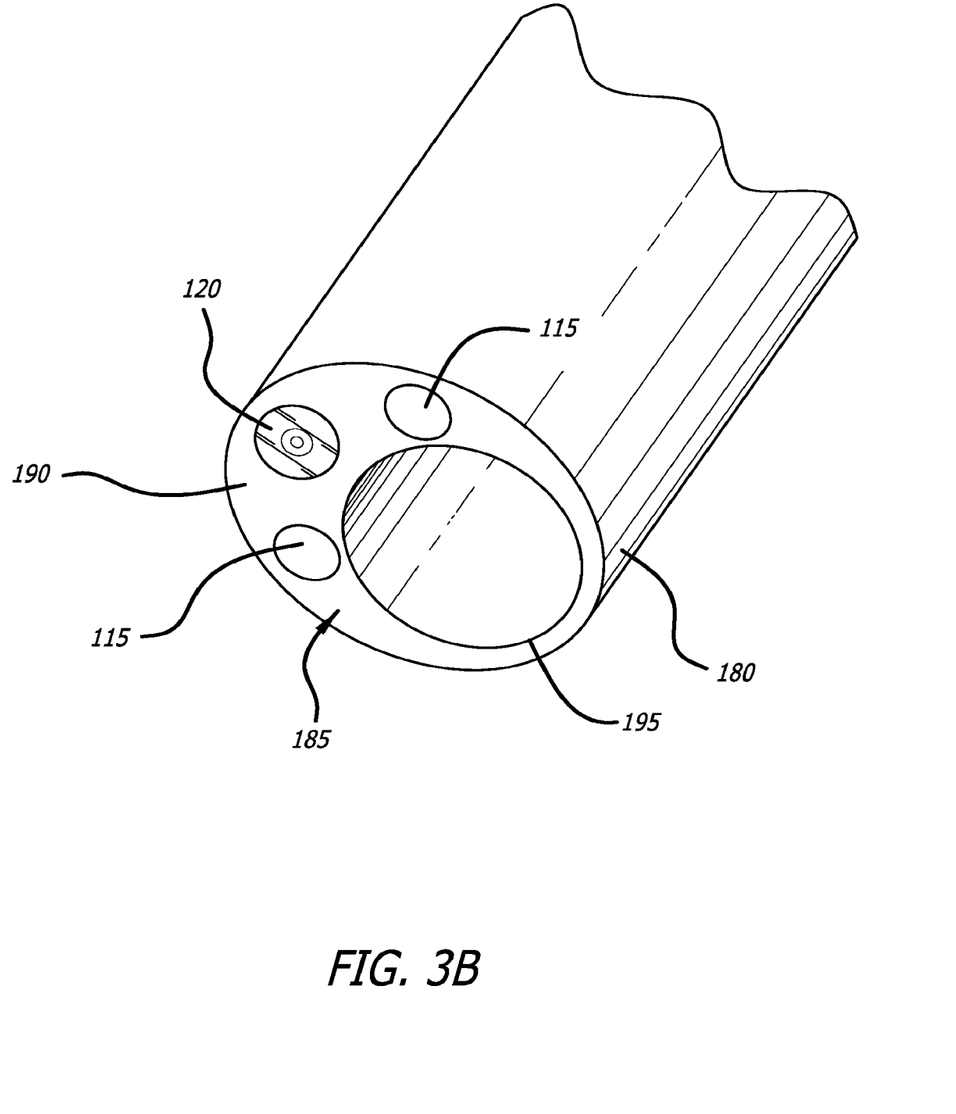
FIG. 3B is an enlarged distal end view of the endoscopic probe of FIG. 3A.

As depicted in FIG. 3A, the tissue detection system 10 or at least the probe 100 may be integrated with an endoscopic probe 170. In this arrangement, the endoscopic probe 170 includes an endoscopic camera 175, an endoscopic probe body 180, and the emitter optical fiber or fibers 115 and the detector optical fibers or fibers 120 are brought into the endoscopic probe body 180 and integrated with endoscope optics 185 at least at a distal end 190 (FIG. 3B) of the endoscopic probe body 180. The endoscopic probe body 180 includes a lumen 195 extending therethrough that terminates at the distal end 190, and the endoscopic camera 175 can visualize a region of interest adjacent the distal end 190 via the lumen 195. This allows for the probing to be done using the endoscopic camera 175 as the guide for placement of the distal end 190 of the endoscopic probe body 180, and correspondingly supports the use of much smaller areas that need to be surgically opened.

Figure 4:
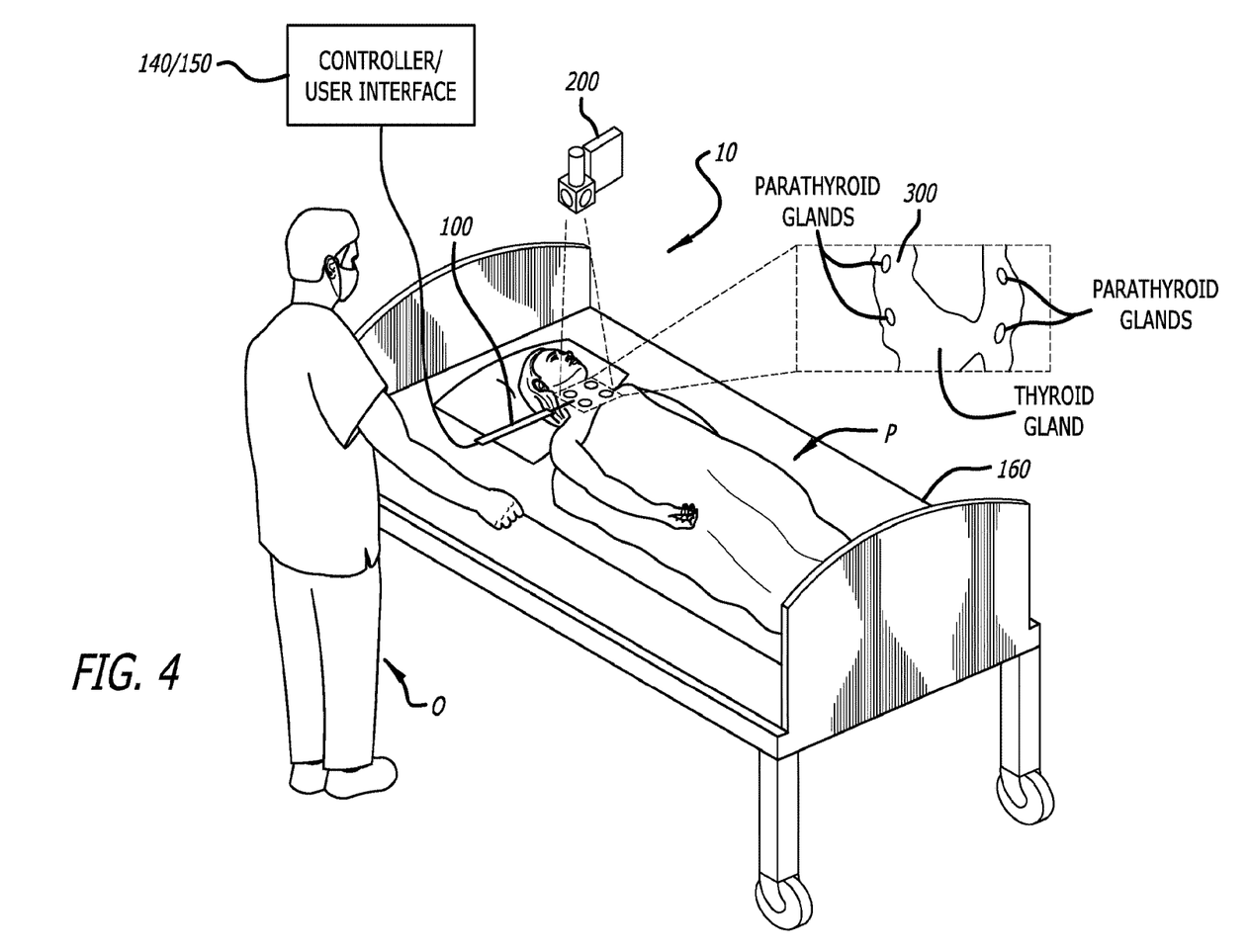
FIG. 4 is an overview of a tissue detection system used with a camera that illustrates the tissue detection system and the camera in relation to a patient and a user, where an internal area of the patient is enlarged and a location of the internal area is indicated for reference.

The probing using the tissue detection system 10 may be enhanced by using an external camera 200 that can be used as a detector to capture radiation from fluorescing tissues of interest, as depicted in FIG. 4. Use of the external camera 200 with the tissue detection system 10 may provide increased illumination and clarity, as opposed to directing by sight the operation of tissue detection system 10, since the external camera 200 can point to potentially fluorescing tissue materials over a larger field of view. In the case of using only the tissue detection system 10 and the probe 100, potential candidates of potentially fluorescing tissue materials will have to be identified by eye and use of the probe 100 facilitates provision of confirmatory information via the fluorescence of the potential candidates. By combining use of the external camera 200 together with the probe 100, an imaged area provided by the external camera 200 can be used to identify candidates of potentially fluorescing tissue materials over a larger field of view, and the probe 100 can then be used for confirmation via fluorescence information acquired from each of those candidates of potentially fluorescing tissue materials by putting the probe in contact or near contact with the surface of the potentially fluorescing tissue materials. The external camera 200 provides an image contrast level that may be helpful but not definitive, while the probe 100 can be used to provide a highly sensitive and quantitative measure, since at each of potentially fluorescing tissue materials, the distal end 135 of the probe body 130 can be positioned in contact or near contact therewith and a definitive indicator of the fluorescence can be obtained and measured. Thus, combining use of the tissue detection system 10 and the probe 100 with the external camera 200 can offer a powerful solution to identify an area or areas of highest fluorescence.

Figure 5A:
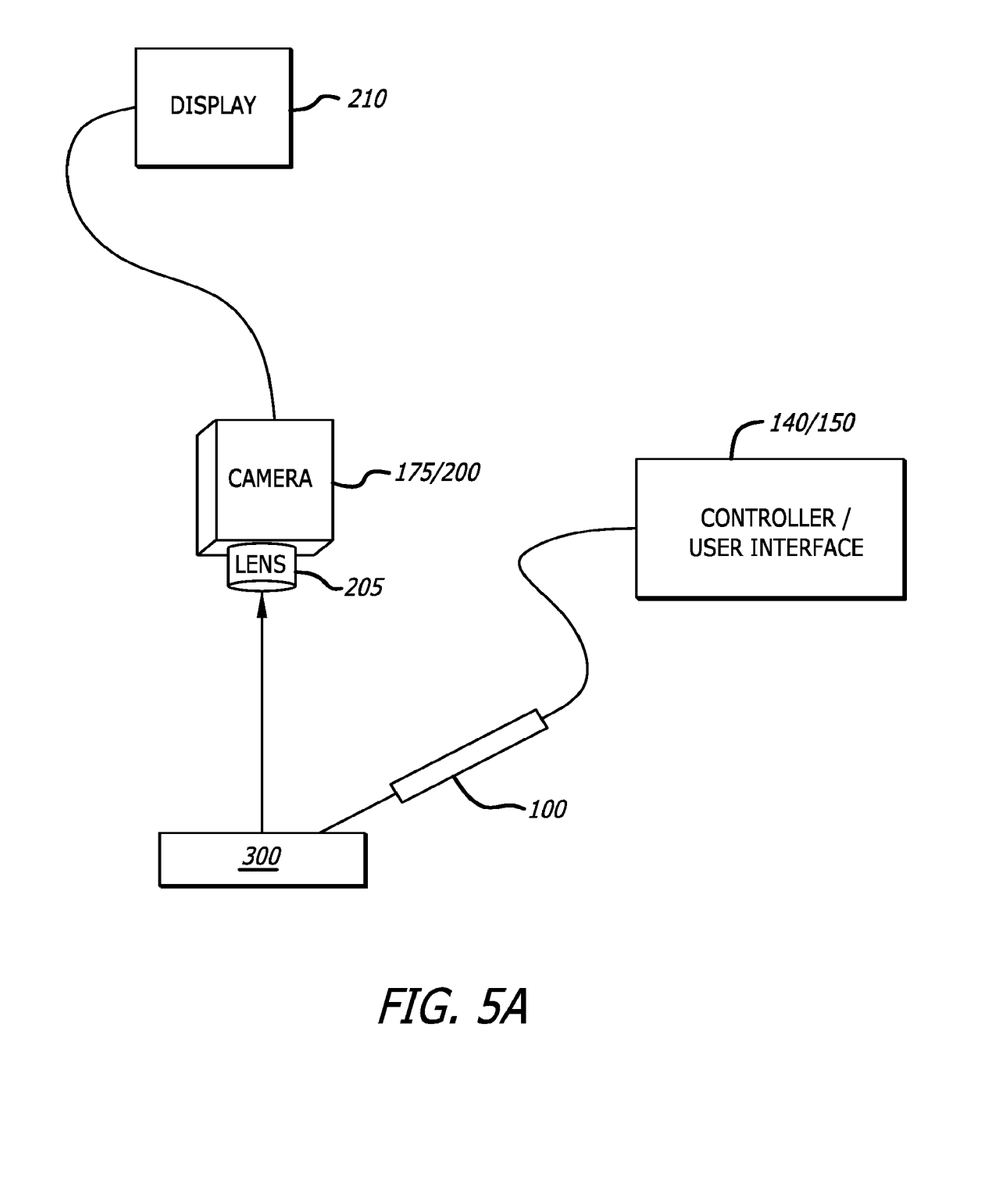
FIG. 5A is a block diagram of a tissue detection system illustrating use of a camera and a corresponding lens.

FIG. 5A shows schematically another arrangement of the tissue detection system 10 with use of a camera, including the endoscopic camera 175, the external camera 200, or otherwise, where camera optics 205 (such as one or more optical lenses and/or filters or the like) and a display 210 (such as a computer monitor/screen) are used with the tissue detection system 10 using the probe 100 and controller/user interface 140/150. Although not shown in FIG. 5A, the emitter 105 can be interposed between the controller/user interface 140/150, and the controller/user interface 140/150 can be used to control operation of the endoscopic camera 175, the external camera 200, and the display 210. Furthermore, the display 210 can be separate from or integrated with the controller 140 and/or the user interface 150.

Figure 5B:
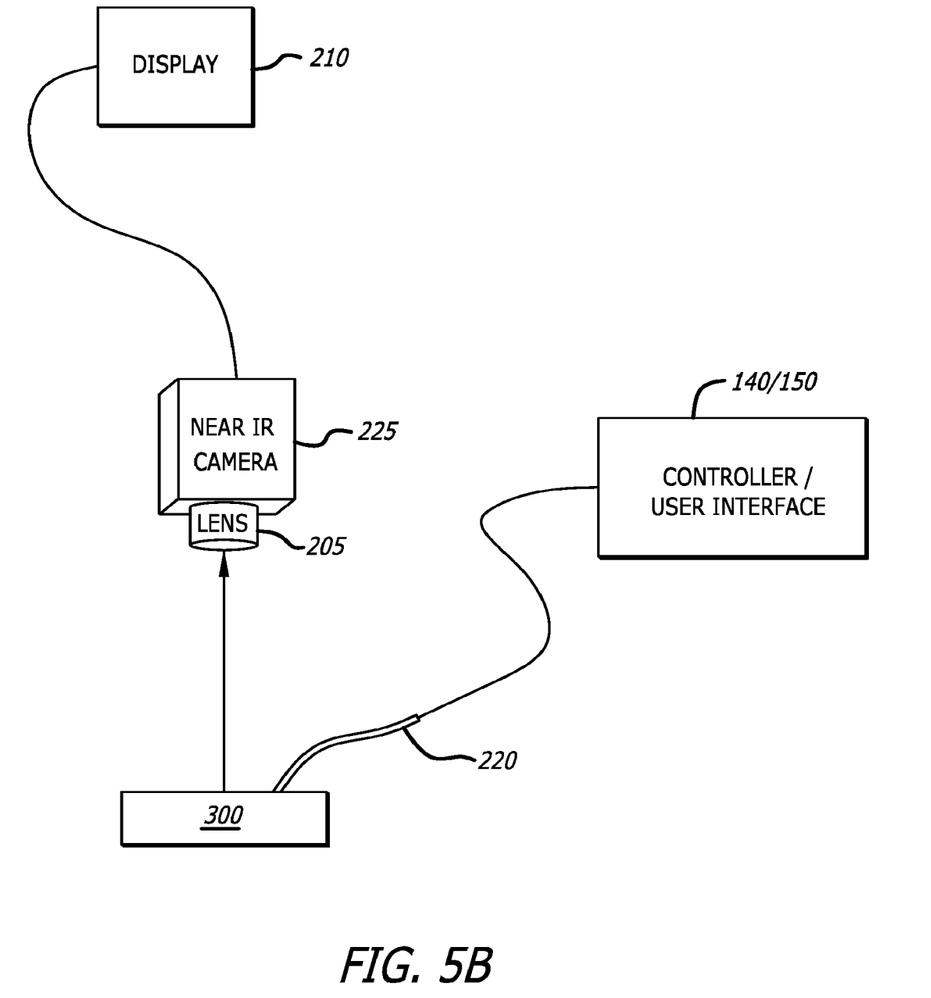
FIG. 5B is a block diagram of a tissue detection system illustrating use of a near infrared camera and a corresponding lens.

FIG. 5B shows schematically yet another arrangement of the tissue detection system 10 using an alternative probe 220 and an alternative camera 225 embodiment, where the probe 220 only provides illumination, and detection is by way of the camera 225. The probe 220 is a hand-held flexible illumination probe that can be positioned in contact or near contact with the surface of the potentially fluorescing tissue materials by the operator O. Furthermore, the camera 225 can be an external near IR camera that is used as a detector to capture radiation from fluorescing tissues of interest. Although not shown in FIG. 5B, the emitter 105 can be interposed between the controller/user interface 140/150, and the controller/user interface 140/150 can be used to control operation of the camera 225 and the display 210. Furthermore, the display 210 can be separate from or integrated with the controller 140 and/or the user interface 150.

The probe 220 can be brought into contact or near contact with the potentially fluorescing tissue materials or at any desired angle relative to the tissue in which fluorescence is being excited. Use of the probe 220 enables the illumination/stimulation of a region of interest where illumination would normally not reach. However, the fluorescence stimulated in the tissues of interest may be hard to view with the detector optical fiber or fibers 120 incorporated in the probe body 130. Examples of this would be sub-surface regions, where the fluorescence is usually too weak to be detected with the detector optical fiber or fibers 120. Other examples would be fluorescing tissue materials at the boundary or just outside the boundary of the field of view of the detector optical fiber or fibers 120. The probe 220 brings the light source close to the region of interest, which in turn increases the fluorescence emitted and enables the camera 225 to view and capture it. And the external camera 225 can point to potentially fluorescing tissue materials over a larger field of view including the entire region of interest. The probe 220 can include only illumination fibers, and as few as one fiber, that are chosen to maximize the transmission of radiation therefrom. This illumination fiber or fibers can also have a one or more lenses and/or filters or the like at its end or ends (ultimately oriented towards the tissue) that can eliminate any fluorescence emitted by the fiber materials in response to the illumination.

Where the illumination/stimulation is accomplished with the hand-held illumination probe 220, but the detection is accomplished by looking at an image of the entire region of interest using, for example, the camera 225, the problem of background light from, for example, operating room lights is different from the case where the illumination and detection are both accomplished at the distal end 135 of the probe 100. Since the camera 225 essentially is the equivalent to a multiplicity of detectors in parallel, and the area of the fluorescence may be anywhere within the imaged area, the demodulation techniques described above cannot be applied directly.

Figure 6:
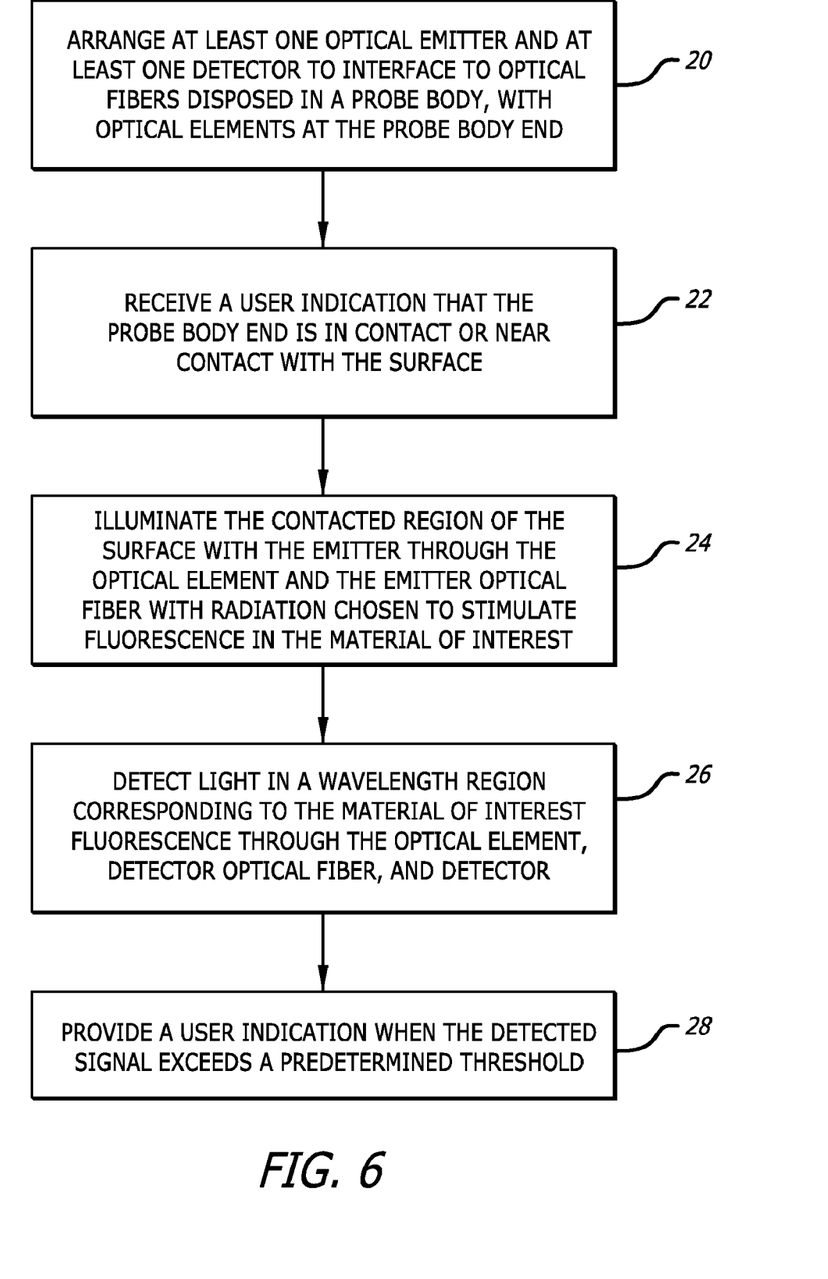
FIG. 6 is a flowchart illustrating a method for tissue detection.

FIG. 6 illustrates an embodiment of a method for use of the tissue detection system 10. First, at 20, the probe 100 is provided, and the probe 100 includes the emitter optical fiber or fibers 115 and the detector optical fiber or fibers 120 extending therethrough to the distal end of the probe body 135. At 22, the operator O receives an indication (visual or otherwise) that the distal end 135 of the probe body 130 is in contact or near contact with the surface of the potentially fluorescing tissue materials. At 24, the potentially fluorescing tissue materials are illuminated with the radiation from the emitter 105 via the optical element(s) 125 and the emitter optical fiber or fibers 115. At 26, the fluorescence (if any) is detected by the detector 110 via the optical element(s) 125 and the detector optical fiber or fibers 120. At 28, the controller 140 and/or the user interface 150 can provide an indication when the fluorescence detected by the detector 110 exceeds the threshold. Steps 24, 26, and 28 can also be performed with the other embodiments disclosed herein.

Figure 7:
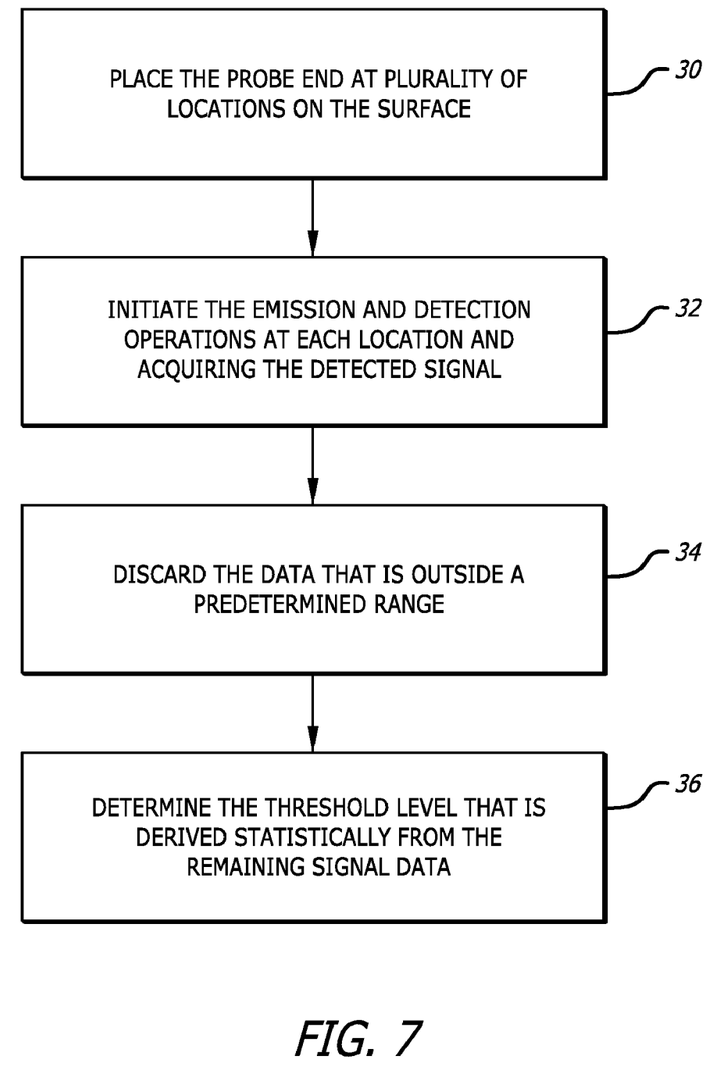
FIG. 7 is a flowchart illustrating a method of calibration to facilitate tissue detection.

FIG. 7 illustrates an embodiment of a method used to calibrate the tissue detection system 10. First, at 30, the distal end 135 of the probe body 130 is positioned at various locations on the surface of the potentially fluorescing tissue materials. At 32, the emission and the detection using the emitter 105 and the detector 110, respectively, are initiated at each of the various locations. The detected fluorescence signal corresponding to the fluorescence (if any) that is detected is acquired by the controller 140. At 34, the controller 140 discards any data corresponding to the detected fluorescence signal that is outside a predetermined range. At 36, the threshold level is derived statistically from the remaining data of the corresponding detected fluorescence signal. Thus, using such calibration, threshold levels for the potentially fluorescing tissue materials and other tissues that are clearly different from the potentially fluorescing tissue materials can be obtained. These threshold levels can be used to compute a ratio, and the controller 140 and/or the user interface 150 can provide an indication when the ratio is lower or higher than a threshold ratio. Steps 32, 34, and 36 can also be performed with the other embodiments disclosed herein.

Figure 8:
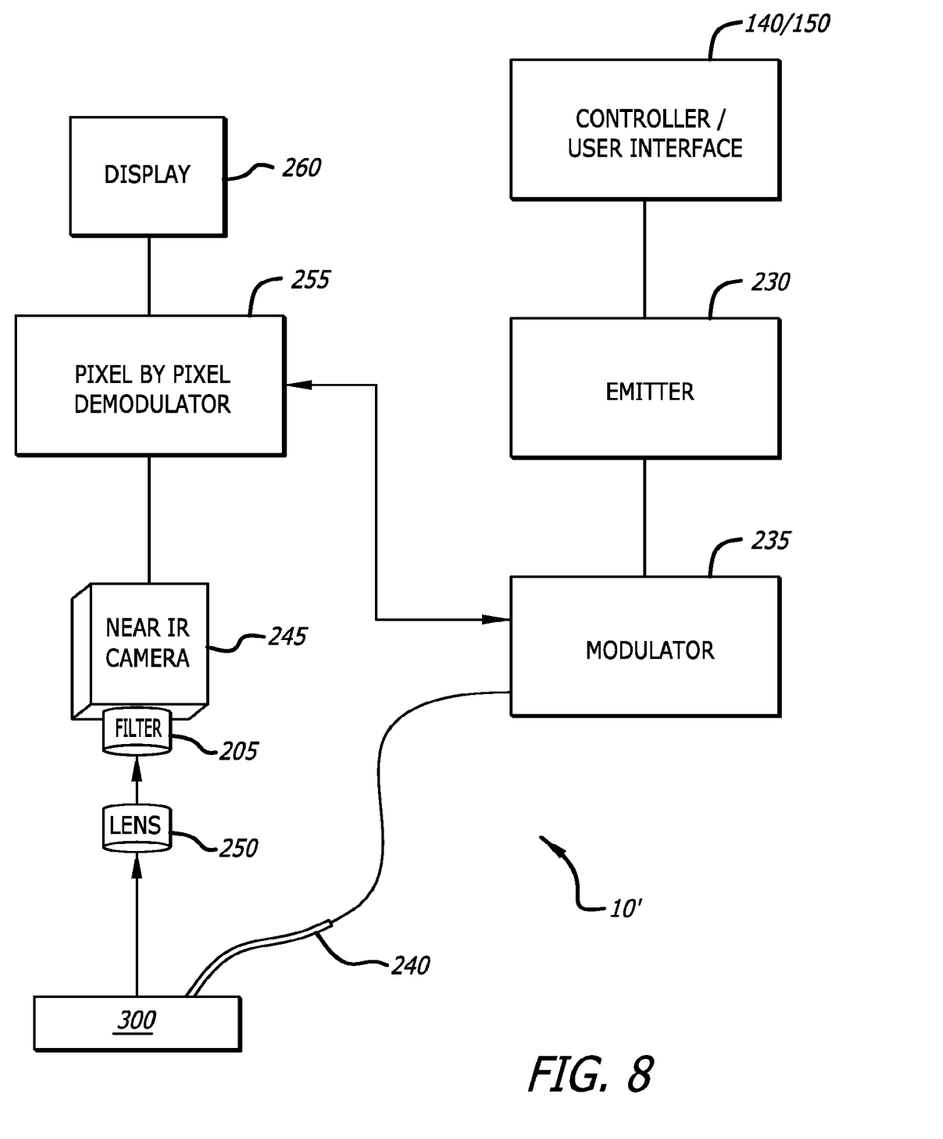
FIG. 8 is a block diagram of a tissue detection system using a near infrared camera with pixel by pixel demodulation.

Referring to FIG. 8, an alternative embodiment of the tissue detection system generally referenced by the numeral 10' is shown. The tissue detection system 10' includes an emitter 230 (that can be similar to the emitter 105) such as a solid state laser, a laser diode, or other suitable source that can be configured to emit radiation at a selected wavelength, and that can be modulated by a modulator 235 to alter the emitted radiation lower or higher. The modulator 235 may be of a variety of types such as a chopper, pockel cell, acoustic optical modulator, or other light modulation device. A modulated emitter signal is delivered from the emitter 230 through the modulator 235 to a probe 240 (that can be similar to the alternative probe 220), and a modulated probe signal from the probe 240 is applied to a region of interest. Thereafter, a near IR camera 245 with or without use of camera optics 250 (such as one or more optical lenses and/or filters or the like) views the region of interest. The near IR camera 245 can be used as a detector to capture radiation from fluorescing tissues of interest. A signal from the near IR camera 245 can be passed through a demodulator 255, which also can use a modulator frequency from the modulator 235 as an input, before a demodulated signal from the demodulator 255 is passed onto a display 260. Like the display 210, the display 260 can be separate from or integrated with the controller 140 and/or the user interface 150.

The demodulator 255 may be in the form of a fast digital processor such as a graphics or gaming processor, or a FPGA (field-programmable gate array), that is capable of performing large numbers of fast parallel processing algorithms. Successive frames of images from the near IR camera 245 are subjected to pixel by pixel demodulation functions, i.e., each pixel is demodulated by the fast parallel processor by the demodulator. Pixel by pixel demodulation functions may included digital lock-in to the modulation frequency, or Fourier transform demodulation.

A rolling window of demodulated video frames may be continuously passed on to the display 260 for display from the demodulator 255, which results in a slight startup delay and then real time demodulated video that has very high gain on the emitted light stimulated by the modulated probe signal and high rejection of background illumination from, for example, the operating room lights.

In one embodiment, the near IR camera 245 may include outputs that correspond directly to the fluorescence detected by each detector in a camera imaging array of the near IR camera 245. For this case, luminance values for the detected fluorescence may be parsed by pixel, and the demodulation function performed in parallel in the fast digital processor of the demodulator 255. In one embodiment. a Nvidia Tegra processor can be programmed to parse and perform a digital lock-in operation on hundreds of pixels in parallel at video rates.

Figure 9:
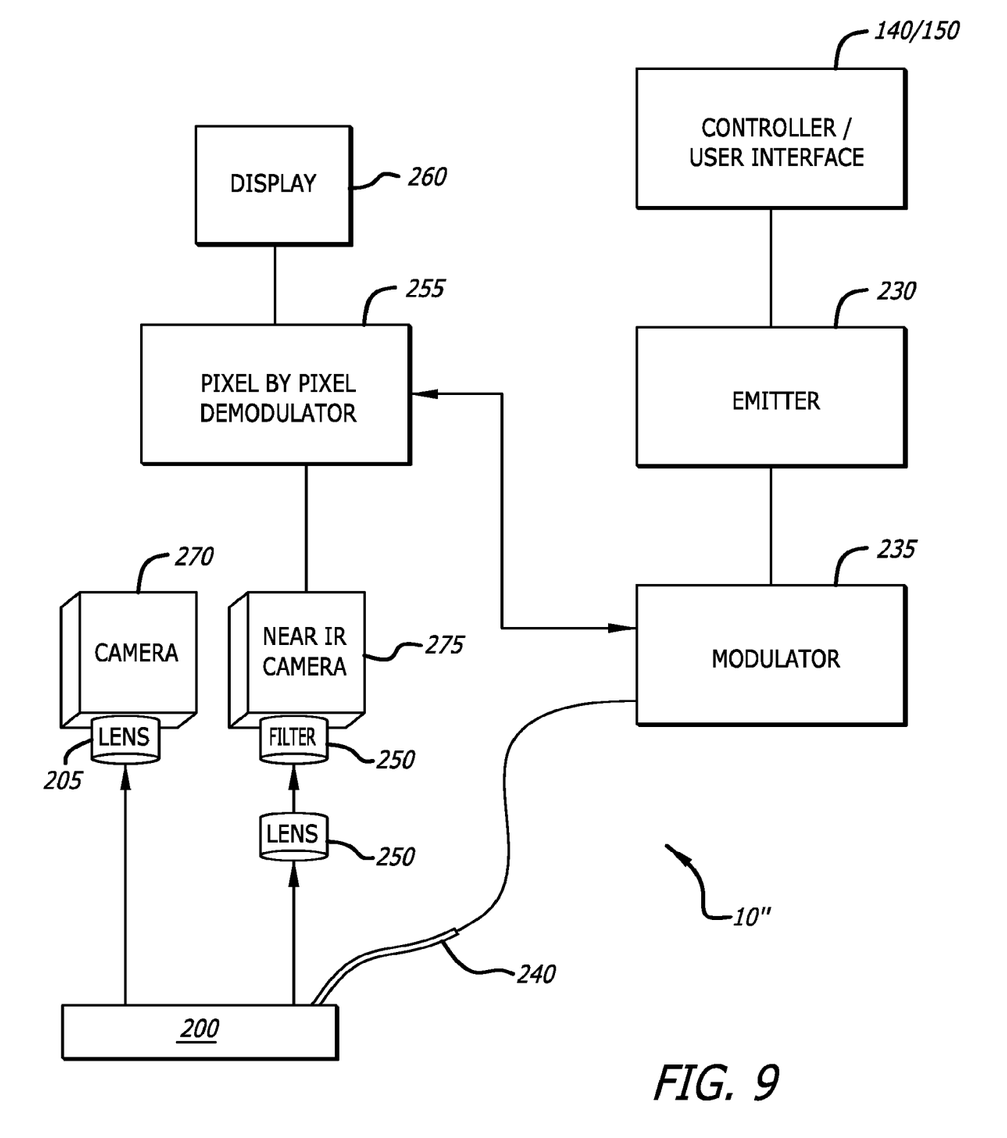
FIG. 9 is a block diagram of a tissue detection system using a camera and a near infrared camera with pixel by pixel demodulation.

In FIG. 9, an alternative embodiment of the tissue detection system referenced by the numeral 10" is shown. The tissue detection system 10" is similar to the tissue detection system 10', but the tissue detection system 10" instead employs a standard video camera 270 (that can employ the camera optics 205) and a near IR camera 275 (that can employ the camera optics 250) that both image an identical region of interest. The near IR camera 275 can be used as a detector to capture radiation from fluorescing tissues of interest. In this embodiment, the pixel lock-in is performed on output from the near IR camera 275 by the demodulator 255, and pixels that meet predetermined criteria are mixed with output from the standard video camera 270 by the demodulator 255 to produce a highlighting of video from the standard video camera 270 for pixels showing fluorescence in an image ultimately displayed on the display 260.

Various aspects of the embodiments may include any combination of processing elements and memory that may include computing devices executing software routines, such devices including computers and personal-electronic devices, as well as programmable electronics, logic circuits, and other electronic implementations. Various combinations of optical elements may be employed including lasers, LED's, and other light sources, filters, lenses, mirrors, beamsplitters, and the like. The details of the optical, electronic, and processing embodiments described herein are illustrative and are not intended as limiting as alternative approaches using other combinations of like elements may be used to accomplish the same results in essentially the same manner.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

The invention claimed is:

1. A tissue detection system for locally stimulating fluorescence in a surgical region, and locating fluorescing areas in the surgical region, comprising:
   a probe having a distal end configured for placement in contact or near contact with tissue material of interest;
   at least one emitter and at least one emitter optical fiber, the at least one emitter configured to emit radiation for stimulating fluorescence in the tissue material of interest, the at least one emitter optical fiber coupled to the at least one emitter and extending through at least a portion of the probe;
   at least one detector and at least one detector optical fiber, the at least one detector configured to detect fluorescence from the tissue material of interest within a local field of view, the at least one detector optical fiber coupled to the at least one detector and extending through at least a portion of the probe;
   at least one camera separate from the probe and configured to detect fluorescence from the tissue material of interest within a wide field of view;
   a controller and user interface coupled to the at least one emitter and configured to initiate operation of the at least one emitter, wherein distal ends of the at least one emitter optical fiber and the at least one detector optical fiber are collocated with the distal end of the probe, the at least one emitter optical fiber is configured to transfer the radiation from the at least one emitter to the distal end thereof, and the at least one detector optical fiber is configured to transfer a signal corresponding to the fluorescence from the tissue material of interest within the local field of view to the at least one detector; and
   at least one modulator configured to modulate the radiation from at least one of the at least one emitter, and at least one demodulator configured to demodulate the signal corresponding to the fluorescence detected with the camera, wherein the signal corresponding to the fluorescence detected with the camera is demodulated by the demodulator on a pixel-by-pixel basis.

2. The tissue detection system of claim 1, wherein the tissue material of interest is parathyroid tissue.

3. The tissue detection system of claim 2, wherein at least one of the at least one emitter includes a narrowband radiation source whose frequency is centered on 785 nm plus or minus 10 nm.

4. The tissue detection system of claim 3, further comprising a filter further limiting emitter bandwidth, and wherein at least one of the at least one emitter is a solid-state laser or a laser diode.

5. The tissue detection system of claim 4, wherein at least one of the at least one detectors is a near IR camera with a high pass filter, and wherein the high pass filter is configured to pass optical wavelengths above emitted wavelengths of the at least one emitter.

6. The tissue detection system of claim 5, wherein the high pass filter is configured to pass optical wavelengths above 800 nm.

7. A tissue detection system for locally stimulating fluorescence in a surgical region, and locating fluorescing areas in the surgical region, comprising:
a probe having a distal end configured for placement in contact or near contact with tissue material of interest;
at least one emitter and at least one emitter optical fiber, the at least one emitter configured to emit radiation for stimulating fluorescence in the tissue material of interest, the at least one emitter optical fiber coupled to the at least one emitter and extending through at least a portion of the probe;
at least one IR camera separate from the probe and configured to capture radiation from the tissue material of interest as the tissue material of interest fluoresces;
a controller and user interface coupled to the at least one emitter and configured to initiate operation of the at least one emitter, the at least one emitter optical fiber configured to transfer the radiation from the at least one emitter to the distal end thereof; and
at least one modulator configured to modulate the radiation from at least one of the at least one emitter, and at least one demodulator configured to demodulate the signal corresponding to the tissue fluorescence detected with the IR camera, wherein the signal corresponding to the fluorescence detected with the IR camera is demodulated by the demodulator on a pixel-by-pixel basis.

8. The tissue detection system of claim 7, wherein the tissue material of interest is parathyroid tissue.

9. The tissue detection system of claim 7, wherein at least one of the at least one emitter includes a narrowband radiation source whose frequency is centered on 785 nm plus or minus 10 nm.

10. The tissue detection system of claim 9, further comprising a filter further limiting emitter bandwidth, and wherein at least one of the at least one emitter is a solid state laser or a laser diode.

11. The tissue detection system of claim 10, wherein the IR camera is a near IR camera with a highpass filter, and wherein the highpass filter is configured to pass optical wavelengths above emitted wavelengths of at least one of the at least one emitter.

12. The tissue detection system of claim 11, wherein the highpass filter is configured to pass optical wavelengths above 800 nm.

* * * * *